United States Patent
Simard

(10) Patent No.: US 10,899,833 B2
(45) Date of Patent: *Jan. 26, 2021

(54) HUMAN ANTIBODY SPECIFIC FOR INTERLEUKIN-1 ALPHA

(71) Applicant: Janssen Biotech, Inc., Horsham, PA (US)

(72) Inventor: John Simard, Austin, TX (US)

(73) Assignee: Janssen Biotech, Inc., Horsham, PA (US)

( * ) Notice: Subject to any disclaimer, the term of this patent is extended or adjusted under 35 U.S.C. 154(b) by 35 days.

This patent is subject to a terminal disclaimer.

(21) Appl. No.: 15/789,774

(22) Filed: Oct. 20, 2017

(65) Prior Publication Data

US 2018/0127495 A1 May 10, 2018

Related U.S. Application Data

(60) Continuation of application No. 14/877,964, filed on Oct. 8, 2015, now Pat. No. 9,840,558, which is a continuation of application No. 14/567,072, filed on Dec. 11, 2014, now Pat. No. 9,181,338, which is a continuation of application No. 14/177,892, filed on Feb. 11, 2014, now Pat. No. 8,956,831, which is a continuation of application No. 13/762,453, filed on Feb. 8, 2013, now Pat. No. 8,679,489, which is a continuation of application No. 13/224,943, filed on Sep. 2, 2011, now Pat. No. 8,388,956, which is a division of application No. 12/455,458, filed on Jun. 1, 2009, now Pat. No. 8,034,337.

(60) Provisional application No. 61/178,350, filed on May 14, 2009, provisional application No. 61/121,391, filed on Dec. 10, 2008, provisional application No. 61/057,586, filed on May 30, 2008.

(51) Int. Cl.

| C07K 16/24 | (2006.01) |
| A61K 39/395 | (2006.01) |
| C12N 5/071 | (2010.01) |
| G01N 33/68 | (2006.01) |
| C12N 5/09 | (2010.01) |
| C07K 14/545 | (2006.01) |
| C07K 14/54 | (2006.01) |
| A61K 39/00 | (2006.01) |

(52) U.S. Cl.
CPC .......... *C07K 16/245* (2013.01); *C07K 14/545* (2013.01); *C12N 5/069* (2013.01); *C12N 5/0693* (2013.01); *G01N 33/6863* (2013.01); *G01N 33/6869* (2013.01); *A61K 39/3955* (2013.01); *A61K 2039/55527* (2013.01); *C07K 14/5412* (2013.01); *C07K 16/24* (2013.01); *C07K 2317/14* (2013.01); *C07K 2317/21* (2013.01); *C07K 2317/24* (2013.01); *C07K 2317/76* (2013.01); *C07K 2317/92* (2013.01); *C12N 2330/50* (2013.01); *G01N 2333/545* (2013.01)

(58) Field of Classification Search
None
See application file for complete search history.

(56) References Cited

U.S. PATENT DOCUMENTS

| 4,968,607 | A | 11/1990 | Dower |
| 5,959,085 | A | 9/1999 | Garrone et al. |
| 8,388,956 | B2* | 3/2013 | Simard .................... A61P 37/00 424/130.1 |
| 8,388,969 | B2* | 3/2013 | Simard ................ C12N 5/0693 424/145.1 |
| 8,679,489 | B2* | 3/2014 | Simard .................... A61P 43/00 424/130.1 |
| 8,784,817 | B2* | 7/2014 | Simard .............. G01N 33/6863 424/145.1 |
| 9,840,558 | B2* | 12/2017 | Simard .................. C12N 5/069 |
| 2003/0004061 | A1 | 1/2003 | Kraemer |
| 2003/0023205 | A1 | 1/2003 | Botich et al. |
| 2005/0005401 | A1 | 1/2005 | Bae |

FOREIGN PATENT DOCUMENTS

| CN | 1662557 | 8/2005 |
| WO | 2007135546 | 11/2007 |

OTHER PUBLICATIONS

Kurzrock et al, OncoImmunology Journal, 2019, vol. 8, No. 3, pp. 1-7.*
Hong et al, The Lancet, 2014, vol. 15, pp. 656-666.*
Chang, C.H. et al., "Interleukin-1alpha released from epithelial cells after adenovirus type 37 infection activates intercellular adhesion molecule 1 expression on human vascular endothelial cells," Journal of Virology, Jan. 2002, vol. 76, No. 1:427-431.
Lundberg, Ingrid et al., "Cytokine production in muscle tissue of patients with idiopathic inflammatory myopathies," Arthritis & Rheumatism, May 1997, vol. 40, No. 5:865-874.
Tsunoda, Yasuaki et al., "Immunohistochemical study of cytokines and extracellular matrices at invasive sites of human colon cancers," Biotherapy, May 1996, vol. 10, No. 5:789-790; Abstract only.
Garrone P et al, "Generation and characterization of a human monoclonal autoantibody that acts as a high affinity interleukin-1 alpha specific inhibitor", Molecular Immunology, Pergamon, vol. 33, No. 7-8, pp. 649-658, 1996.
Wood D D et al, "Release of Interleukin-1 From Human Synovial Tissue In-Vitro", Arthritis and Rheumatism, vol. 28, No. 8, pp. 853-862, 1985.

(Continued)

*Primary Examiner* — Bridget E Bunner
*Assistant Examiner* — Fozia Hamud
(74) *Attorney, Agent, or Firm* — Ice Miller LLP

(57) ABSTRACT

Fully human monoclonal Abs includes (i) an antigen-binding variable region that exhibits very high binding affinity for IL-1α and (ii) a constant region that is effective at both activating the complement system though C1q binding and binding to several different Fc receptors.

12 Claims, No Drawings

Specification includes a Sequence Listing.

(56) References Cited

OTHER PUBLICATIONS

Vazquez A et al, "Interleukin 1 can replace monocytes for the specific human B-cell response to a particulate antigen", Cellular Immunology, Academic Press, San Diego, CA, US, vol. 86, No. 2, pp. 287-298, 1884.
Jefferis Roy, "Antibody therapeutics: isotype and glycoformselection", Expert Opinion on Biological Therapy, vol. 7, No. 9, ISSN 1471-2598, pp. 1401-1413, 2007.
Miossec P, "Anti-interleukin 1alpha autoantibodies.", Annals of the Rheumatic Diseases, vol. 61, No. 7, ISSN 0003-4967, pp. 577-579, 2002.
Salfeld Jochen G, "Isotype selection in antibody engineering.", Nature Biotechnology, vol. 25, No. 12, ISSN 1546-1696, Págs. 1369-1372, 2007.
Niki et al., "Membrane-associatged IL-1 contributes to chronic synovitis and cartilage destruction in human IL-1 alpha transgenic mice.", J Immunology, vol. 172, Págs. 577-584, 2004.
Mchale et al., "TNF-alpha and IL-1 sequentially induce endothelial ICAM-1 and VCAM-1 expression in MRL/lpr lupus-prone mice.", J Immunology, vol. 163, Págs. 3993-4000, 1999.
Sandborg et al., "Modulation of IL-1 alpha, IL-1 beta, and 25K Mr non-IL-1 activity released by human mononuclear cells.", J Leukocyte Biology, vol. 46, Págs. 417-427, 1989.
Genbank, Database accession No. AY510107.1 DOI: https://www.ncbi.nlm.nih.gov/nuccore/AY510107.1, 2005.
Svenson et al., "Binding of Cytokines to Pharmaceutically Prepared Human Immunoglobulin," J. Clin. Invest., 92:2533-2539, 1993.
Amicon Ultra2001; Millipore technical datasheet; 9 pages.
Apte, Ron N., et al., Effects of micro-environment- and malignant cell-derived interleukin-1 in carcinogenesis, tumour invasiveness and tumour-host interactions, European Journal of Cancer, 2006, vol. 42:751-759.
Barkley, D.E.H. et al: "Cells with dendritic morphology and bright interleukin-1 alpha staining circulate in the blood of patients with rheumatoid arthritis," Clin.Exp.Immmunol., 1990, vol. 80:25-31.
Beasley, Debbie and Angela L. Cooper: "Constitutive expression of interleukin-1 alpha precursor promotes human vascular smooth muscle cell proliferation," American Physiological Society, 1999, No. 276:H901-H912.
Belge, Kai-Uwe et al., The Proinflammatory CD14+ CD16+DR++ Monocytes Are a Major Source of TNF1, The Journal of Immunology, 2002, vol. 168:3536-3542.
Bendtzen, Klaus et al., Detection of Autoantibodies to Cytokines, Molecular Biotechnology, 2000, vol. 14, 14 pages.
Bendtzen, Klaus et al., High-Avidity Autoantibodies to Cytokines, Trends Immunology Today, May 1998, vol. 19, No. 5 209, 3 pages.
Boselli, Joseph et al: Fibronectin: Its relationshp to basement membranes, Light Microscopic Studies, Cell.Res., vol. 5, 1981:391-404.
Braddock, M. et al., Therapeutic potential of targeting IL-1 and IL-18 in inflammation, Expert Opin. Biol. Ther., 2004, vol. 4, No. 6:8476-860.
Buchan, G. et al: "Interleukin-1 and tumour necrosis factor mRNA expression in rheumatoid arthritis: prolonged production of IL-1alpha," Clin. Exp. Immunol. (1988), vol. 73:449-455.
Campbell et al. Theriology, 1997, vol. 47, No. 1, pp. 63-72.
Chamberlain, R.S. et al., Innovations and strategies for the development of anticancer vaccines, Exp. Opin. Pharmacother., 2000, vol. 1(4)603-614.
Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.
Clinical Trial Review: "Acne," Journal of Drugs in Dermatology (JD online Today), Jun. 2012, vol. 11, Issue 6:1-3; <<http://jddonline.com/articles/dermatology/S1545961612P0780X/1>>, last visited on Jan. 17, 2017.

Clinical Trial Review: Acne; <<http://jddonline.eom/articles/dermatology/S1545961612P0780X/1>>, last visited on Oct. 16, 2014; 3 pages.
Clinton Steven K. et al., Interleukin-1 gene expression in rabbit vascular tissue in vivo, American Journal of Pathology, Apr. 1991, vol. 138, No. 4:1005-1014.
Costelli, Paola et al: "Interleukin-1 receptor antagonist (IL-1ra) is unable to reverse cachexia in rats bearing an ascites hepatoma (Yoshida AH-130)," Cancer Letters 95, 1995, pp. 33-38.
Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.
Dekker, S.K. et al: "Characterization of interleukin-1alpha-induced melanoma cell motility: inhibition by type I and type II receptor-blocking monoclonal antibodies," Melanoma Research, 1997, vol. 7:223-230.
Dinarello, Charles A. et al., Anticytokine strategies in the treatment of the systemic inflammatory response syndrome, The Journal of the American Medical Association, Apr. 1993, vol. 269, No. 14:1829-1835.
Dinarello, Charles A., Biologic basis for interleukin-1 in disease, Blood, Mar. 1996, vol. 87, No. 6:2095-2147.
Dinarello, Charles A., Modalities for reducing interleukin 1 activity in disease, TiPS, May 1993 vol. 14:155-159.
Dinarello, Charles A., The role of interleukin-1 in disease, The New England Journal of Medicine, 1993, vol. 328, No. 2:106-113.
Dinarello, Charles A., Therapeutic strategies to reduce IL-1 activity in treating local and system inflammation, Current Opinion in Pharmacology, 2004, vol. 4:378-385.
El-Osta, Hazem et al.: "Successful treatment of Castleman's Disease with Interleukin-1 receptor antagonist (Anakinra)," Molecular Cancer Therapy, 2010, vol. 9:1485-1488.
Eugui et al. (1990) PNAS 87: 1305-1309.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
Feldman et al., American Family Physician, 69(9):2123-30, 2004.
Fong Y; Moldawer L L; Marano M; Wei H; Barber A; Manogue K; Tracey K J; Kuo G; Fischman D A; Cerami A; et al., "Cachectin/TNF or IL-1 alpha induces cachexia with redistribution of body proteins.", American Journal of Physiology, American Physiological Society, US, US, (Mar. 1, 1989), vol. 256, No. 3, ISSN 0002-9513, pp. R659-R665, XP009184008.
Francois Mach., "Toward New Therapeutic Strategies Against Neointimal Formation in Restenosis", Arterioscler Thromb Vasc Biol, (2000), vol. 20, pp. 1699-1700, XP055244035.
Fujii, Masakazu et al.: "A case of advanced gastric cancer with carcinomatous ascites successfully treated with intraperitoneal administration of CDDP and TS-1," Japanese Journal of Gastoenterological Surgery, 2006, vol. 39:189-195.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.
GE Healthcare Instructions, 2005, 12 pages.
Genbank, (May 19, 2005), Database accession No. AY510107.1, XP008146519.
Gonzalez-Lopez, M.A. et al: "New-onset psoriasis following treatment with the interleukin-1 receptor antagonist anakinra," British Journal of Dermatology, May 2008, vol. 158, No. 5:1146-1148.
Griffiths, Andrew D. et al., Human anti-self antibodies with high specificity from phage display libraries, the EMBO Journal, 1993, vol. 12, No. 2:725-734.
Hansen, M. B. et al., Sex- and age-dependency of IgG autoantibodies against IL-1 alpha in healthy humans, European Journal of Clinical Investigation, 1994, vol. 24:212:218.
Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.

(56) References Cited

OTHER PUBLICATIONS

Heine, GH., et al., CD14++CD16+ monocytes but not total monocyte numbers predict cardiovascular events in dialysis patients, Kidney International, 2008, vol. 73:622-629.
Heyderman, R.S. et al.: "Modulation of the endothelial procoagulant response to lipoploysaccharide and tumour necrosis factor-alpha in-vitro: The effects of dexamethasone, pentoxifylline, iloprost and a polyclonal anti-human IL-1alpha antibody," Inflamm Res, vol. 44, 1995:275-280.
Hoge, E.A. et al: "Broad spectrum of cytokine abnormalities in panic disorder and posttraumatic stress disorder," Depression and Anxiety, vol. 26, No. 5, May 2009:447-455; Abstract only.
Hong, David S. et al: "Abstract A211: A phase I study of MABp1, a first-in-human, first-true human monoclonal antibody against the II-1 in patients with advanced cancer," Molecular Cancer Therapeutics, 2011, (1 page).
Horai, R. et al., Production of mice deficient in genes for interleukin (1L)-1alpha, IL-1beta,IL-1alpha/beta, and IL-1 receptor antagonist shows that IL-1 beta is crucial in turpentine-induced fever development and glucocorticoid secretion, J. Exp. Med, 1998, vol. 187, No. 9:1463-1475.
Immunobiology, Janeway et al., The immune system in health and disease, 3rd edition, 1997section 3.4 and figure 3.4, 9 pages.
Ito, R. et al., Interleukin 1alpha acts as an autocrine growth stimulator for human gastric carcinoma cells, Cancer Research, Sep. 1993, vol. 53:4102-4106.
Iwahashi, Mitsuhiro et al., Expression of Toll-Like Receptor 2 on CD16+ Blood Monocytes and Synovial Tissue Macrophages in Rheumatoid Arthritis, Arthritis and Rheumatism, 2004, vol. 50, No. 5:1457-1467.
Janeway, C.A., Jr. et al, The induction, measurement, and manipulation of the immune response, ImmunoBiology, the Immune System in Health and Disease, 1997, Third Edition, 8 pages.
Janik, John E. et al: "Interleukin 1alpha increases serum leptin concentrations in humans," Journal of Clinical Endocrinology and Metabolism, vol. 92, No. 9, 1997: 3084-3086.
Jefferis, Roy: "Antibody therapeutics: isotype and glycoform selection," Expert Opin. Biol. Ther. (2007) 7 (9):1401-1413.
Joosten, Leo A.B. et al: "Anticytokine Treatment of Established Type II Collagen-Induced Arthritis in DBA/1 MICE," Arthritis & Rheumatism, May 1996, vol. 39, No. 5:797-809.
Joosten, M. et al: "Amelioration of established collagen-induced arthritis (CIA) with anti-IL-1," Agents Actions. vol. 41, Special Conference Issue, 1994:C174-C176.
Jouvenne, P. et al., High levels of neutralizing autoantibodies against IL-1 alpha are associated with a better prognosis in chronic polyarthritis: a follow-up study, Scand. J. Immunol., 1997, vol. 46:413-418.
Kaji, M.: "E-selectin expression induced by pancreas-carcinoma-derived interleukin-1alpha results in enhanced adhesion of pancreas-carcinoma cells to endothelial cells," Mar. 1996, vol. 60Issue 5:712-717(Abstract).
Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.
Kamari et al., BBRC: 405,pp. 197-203 (Year: 2011), 7 pages.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Kanni, T. et al., "MABpl Targeting IL-1a for Moderate to Severe Hidradenitis Suppurativa Not Eligible for Adalimumab: A Randomized Study", Journal of Investigative Dermatology, (Nov. 10, 2017), vol. 138, No. 4, ISSN 1523-1747, pp. 795-801, XP055532244.
Kasahara, T. et al., Preparation and characterization of polyclonal and monoclonal antibodies against human interleukin 1 alpha (IL 1alpha), The Journal of Immunology, Mar. 1987, vol. 138, No. 6:1804-1812.
Kaufman et al Blood, 1999, vol. 94, pp. 3178-3184.

Kaymak, Yesim et al: "Comparison of depression, anxiety and life quality in acne vulgaris patients who were treated with either isotretinoin or topical agents, The International Society of Dermatology," 2009, vol. 48:41-46.
Kishore et al, Immunopharmacology, 2000, vol. 49, pp. 159-170.
Kleiman, et al: "Invasion assays," Current Protocols in Cell Biology, 2001, 12.2.1-12.2.5.
Kumar, Suresh, et al: "Interleukin-1alpha promotes tumor growth and cachexia in MCF-7 xenograft model of breast cancer," American Journal of Pathology, 2003, vol. 163:2531-2541.
Kurokawa, Ichiro et al: "New developments in our understanding of acne pathogenesis and treatment," Experimental Dermatology, vol. 18, 2009:821-832.
Larionov et al., Acta Neuropathol: 113, pp. 33-43 (Year: 2007).
Larrick, James W. et al., Prospects for the therapeutic use of human monoclonal antibodies, Journal of Biological Response Modifiers, 1986, vol. 5:379-393.
Larsen C.M. et al. Interleukin-1-receptor antagonist is type 2 diabetes mellitus. New England Journal of Medicine, 2007, vol. 356, p. 1517-1526.
Larsen, C.M., et al. Sustained effects of interleukin-1 receptor antagonist treatment in type 2 diabetes. Diabetes Care, 2009, vol. 32, p. 1663-1668.
Levetan, C. Oral antidiabetic agents in type 2 diabetes. Current Medical Research and Opinion, 2007, vol. 23, No. 4, p. 945-952.
Li et al, Cancer Research, 2002, vol. 62, pp. 417-423.
Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.
Lindqvist, E. et al., Prognostic laboratory markers of joint damage in rheumatoid arthritis, Ann Rheum Dis, 2005, vol. 64:196-201.
Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.
Ma, Joseph D. et al: "Novel investigational biologics for the treatment of cancer cachexia," Expert Opin. Biol. Ther., 2014, vol. 14(8):1113-1120.
Mach, Francois: "Toward new therapeutic strategies against neointimal formation in restenosis," Arterioscler Thromb Vasc Biol, vol. 20, 2000:1699-1700.
Madeddu, Clelia and Mantovani, Giovanni: "An update on promising agents for the treatment of cancer cachexia," Current Opinion in Supportive and Palliative Care, 2009, vol. 3:258-262.
Mandinov, L. et al.: "Inhibition of in-stent restenosis by oral copper chelation in porcine coronary arteries," Am J Physiol Heart Circ Physiol, 2006, vol. 291:H2692-H2697.
Mariotti, Massimo et al., Iterleukin 1 alpha is a marker of endothelial cellular senescent, Immunity & Ageing, Research, Apr. 2006, vol. 3, No. 4:1-6.
Marques-Deak, Andrea et al: "Measurement of cytokines in sweat patches and plasma in healthy women: Validation in a controlled study," Journal of Immunological Methods, vol. 315, 2006: 99-109.
Merhi-Soussi, F. et al., Interleukin-1 plays a major role in vascular inflammation and atherosclerosis in male apolipoprotein E-knockout mice, Cardiovacular Research, 2006, vol. 66:583-593.
Mizutani, H.: "Endogenous neutralizing anti-IL-1 alpha antibodies in inflammatory skin diseases: possible natural inhibitor for over expressed epidermal IL-1," 1999, Journal of Dermatological Science, vol. 20:63-71.
Morton et al. Crdiovascular Research, vol. 68, pp. 401-501 (Year: 2005).
Morton, Allison, C. et al: "Interleukin-1 receptor antagonist alters the response to vessel wall injury in a porcine coronary artery model," Cardiovascular Research, vol. 68, 2005: 493-501.
Moyeretal., Am. J. Pathol.:138, pp. 951-960 (Year: 1991).
Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.

(56) References Cited

OTHER PUBLICATIONS

Ogushi, F. et al., Autoantibodies to IL-1alpha in sera from rapidly progressive idiopathic pulmonary fibrosis, The Journal of Medical Investigation, 2001, vol. 48:181-189.

Oldenburg, H.S.A., et al. Cachexia and the acute-phase protein response in inflammation are regulated by interleukin-6. Eur. J. Immunol., 1993, vol. 23, p. 1889-1894.

Oriuchi, Noboru et al: "Current status of cancer therapy with radiolabeled monoclonal antibody," Annals of Nuclear Medicine, vol. 19, No. 5, 2005:355-365.

Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.

Patti et al., AM. J. Cardiol: 89., pp. 372-376 (Year: 2002).

Rectenwald et al., "Direct Evidence for Cytokine Involvement in Neointimal Hyperplasia,"; Circulation, vol. 102, pp. 1697-1702, Oct. 3, 2000.

Rhim, JH, et al.: "Cancer cell-derived IL-1 alpha induces Il-8 release in endothelial cells," J Cancer Res Clin Oncol, Jan. 2008, vol. 134(1):45-50. Epub Jul. 11, 2007; (Abstract only).

Ross, C. et al., Increased in vivo antibody activity against interferon alpha, interleuking-1alpha, and interleukin-6 after high-dose Ig therapy, Blood, Sep. 1997, vol. 90, No. 6:2376-2380.

Ross, Christian, et al., High avidity IFN-neutralizing antibodies in pharmaceutically prepared human IgG, J. Clin. Invest., May 1995, vol. 95:1974-1978.

Rossi, Silvia et al.: "Interleukin-1 beta causes anxiety by interacting with the endocannabinoid system," The Journal of Nleuroscience, Oct. 3, 2012, vol. 32, No. 40:13896-13905.

Rubinow, David R. et al: "Reduce anxiety and depression in cystic acne patients after successful treatment with oral isotretinoin," Journal of the American Academy of Dermatology, 1987, vol. 17, No. 1:25-32.

Saitta, P. et al: "An Update on the Presence of Psychiatric Comorbidities in Acne Patients, Part 2: Depression, Anxiety, and Suicide," CUTIS, Aug. 2011, vol. 88:92-97.

Sakurai, T. et al.: "Hepatocyte Necrosis Induced by Oxidative Stress and IL-1alpha Release Mediate Carcinogen-Induced Compensatory Proliferation and Liver Tumorigenesis," Cancer Cell, Aug. 12, 2008, vol. 14:156-165.

Satoh, H. et al., Characterization of anti-IL-1alpha autoantibodies in the sera from healthy humans, Immunopharmacology, 1994, vol. 27:107-118.

Saurat, Jean-Hilaire, et al., Anti-interleukin-1alpoha autoantibodies in humans: Characterization, isotype distribution, and receptor-binding inhibition—Higher frequency in Schnilzler's syndrome (urticaria and macroglobulinemia), J. Allergy Clin. Immunol., Aug. 1991, vol. 88, No. 2:243-256.

Sawai, H. et al: "Interleukin-1alpha enhances the aggressive behavior of pancreatic cancer cells by regulating the alpha 6 beta I-integrin and urokinase plasminogen activator receptor expression," MC Cell Biology, 2006:1-13.

Schlitt, Axel et al., CD14+D16+ monocytes in coronary artery disease and their relationship to serum TNF-alpha levels, Thromb Haemost, 2004, vol. 92:419-424.

Shirakawa, F. et al., Autocrine stimulation of interleukin 1alpha in the growth of adult human T-cell leukemia cells, Cancer Research, Mar. 1989, vol. 49:1143-1147.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

SIGMA Life Science: "Gel Filtration Chromatography," no date; Office Action of U.S. Appl. No. 13/225,029 dated Jun. 19, 2014, 6 pages.

Simard, John: "Early Results from XBiotech's Clinical Study in Cachexia Hint at Breakthrough Treatment," XBiotech News: Clinical Study in Cachex . . . , 2011, (3 pages), (retrieved from the Internet <http://www.xbiotech.com/about/news/early-results-from-xBiotechs-clinical-study-in-cachexia.html>, last visited on Jul. 22, 2015.

Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.

Stark et al., British Journal of Cancer, 83(10):1261-1267, 2000.

Sturlan, Sanda, et al: "In vivo gene transfer of murine interleukin-4 inhibits colon-26-mediated cancer cachexia in mice," Anticancer Research, 2002, vol. 22:2547-2554.

Sunahara, N. et al., Differential determination of recombinant hum interleukin-1 alpha and its deamidated derivative by two sandwhich enzyme immunoassays using monoclonal antibodies. Comparison with a polyclonal antibody-based competitive enzyme immunoassay., J Immunol Methods, 1989, vol. 119:75-82 (Abstract only).

Suzuki, Hiroshi et al., Demonstration of Neutralizing Autoantibodies against Il-1alpha IN sera from patients with rheumatoid arthritis, The Journal of Immunology, Oct. 1, 1990, vol. 145, No. 7:2140-2146.

Svenson M, et al. Cytokine vaccination: neutralising IL-1alpha autoantibodies induced by immunisiation with homologous IL-1alpha. Journal of Immunological Methods, 2000, vol. 236, No. 1-2, p. 1-8.

Svenson, M. et al., Antibody to granulocyte-macrophage colony-stimulating factor is a dominant anti-cytokine activity in human IgG preparations, Blood, Mar. 1998, vol. 91, No. 6:2054-2061.

Svenson, M. et al., Distribution and characterization of autoantibodies to interleukin 1 alpha in normal human sera, Scand. J. Immunol., 1990, vol. 32:695-701.

Svenson, M. et al., Effects of human anti-IL-1alpha autoantibodies on receptor binding and biological activities of IL-1 alpha, Cytokine, Mar. 1992, vol. 4, No. 2:125-133.

Svenson, M. et al., IgG Autoantibodies against Interleuking 1alpha in sera of normal individuals, Scand. J. Immunol., 1989, vol. 29:489-492.

Szabo, K. et al: "Interleukin-1A +4845(G>T) polymorphism is a factor predisposing to acne vulgaris," Tissue Antigens, 2010, vol. 76:411-415.

Tamura, Sumie et al: "Involvement of human interleukin 6 in experimental cachexia induced by a human uterine cervical carcinoma xenograft," Clinical Cancer Research, Nov. 1995, vol. 1:1353-1358.

U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011, 3 pages.

Uefuji, K. et al: "Increased expression of interleukin-1alpha and cyclooxygenase-2 in human gastric cancer: a possible role in tumor progression," 2005, Anticancer Research, vol. 25:3225-3230.

Ulrich, C. et al., Proinflammatory CD14+CD16+ Monocytes are Associated with Subclinical Atherosclerosis in Renal Transplant Patients, American Journal of Transplantation, 2008, vol. 8:103-110.

Van Asseldonk, E.J.P., et al. One week treatment with the IL-1 receptor antagonist anakinra leads to a sustained improvement in insulin sensitivity in insulin resistant patients with type 1 diabetes mellitus. Clinical Immunology, 2015, vol. 160, p. 155-162.

Von Der Thusen, Jan H., et al., Interleukins in atherosclerosis: Molecular pathways and therapeutic potential, Pharmacol Rev, 2003, vol. 55, No. 1:133-166.

Voronov, E. et al: "IL-1 is required for tumor invasiveness and angiogenesis," PNAS, 2003, vol. 100, No. 5:2645-2650.

Waehre et al., Increased expression of interleukin-1 in coronary artery disease with downregulatory effects of HMG-CoA reductase inhibitors, «circ.ahajournals.org», downloaded on Jan. 15, 2008:1966-1972.

Waehreetal., Circulation: 109, pp. 1966-1972 (Year: 2004).

Wake, R. et al., Gender differences in ischemic heart disease, Recent Patents on Cardiovascular Drug Discovery, 2009, vol. 4:234-240.

Wang et al. Nuc. Acids Res. 1999, vol. 27, pp. 4609-4618.

Wigley et al. Reprod Fert Dev, 1994, vol. 6, pp. 585-588.

(56) References Cited

OTHER PUBLICATIONS

Xbiotch IND for the treatment of Chronic Myelogenous Leukemia, pp. 1 (Year: 2010).
XBiotech, Inc. Pressrelease: "XBiotech Files Investigational New Drug (IND) Application with the FDA for the treatment of Chronic Myelogenous Leukemia," Evaluate, Nov. 22, 2010, 2 pages.
Yamada, Takayuki et al.: "Growth Dependency of a new human pancreatic cancer cell line, YAPC, on autocrine interleukin-1 alpha stimulation," Int. J. Cancer, 1998, vol. 76:141-147.
Yanni, G. et al: "Intramuscular gold decreases cytokine expression and macrophage numbers in the rheumatoid synovial membrane," Annals of the Rheumatic Diseases, 1994, vol. 53:315-322.
Yost, J. and J.E. Gudjonsson: "The role of TNF inhibitors in psoriasis therapy: new implications for associated comorbidities," Medicine Reports, May 2009, vol. 1, No. 30:1-4.
Zaragoza et al. (2011), J. of Biomedicine and Biotechnology, vol. 2011, p. 1-13.
Zhu, Y. et al., "The clinical study about interleukin-1 and tumor necrosis factor alpha in hepatocirrhosis," Chinese Journal of Clinical Hepatology, 2001, vol. 17, Issue 4: 233-234.
Ziegler-Heitbrock, Loems, The CD14+CD16+ blood monocytes: their role in infection and inflammation, Journal of Leukocyte Biology, Mar. 2007, vol. 81:584-592.

\* cited by examiner

HUMAN ANTIBODY SPECIFIC FOR INTERLEUKIN-1 ALPHA

CROSS-REFERENCE TO RELATED APPLICATIONS

The present application is a continuation of U.S. nonprovisional patent application Ser. No. 14/877,964 filed on Oct. 8, 2015 (now U.S. Pat. No. 9,840,558), which is a continuation of U.S. nonprovisional patent application Ser. No. 14/567,072 filed on Dec. 11, 2014 (now U.S. Pat. No. 9,181,338), which is a continuation of U.S. nonprovisional patent application Ser. No. 14/177,892 filed on Feb. 11, 2014, (now U.S. Pat. No. 8,956,831), which is a continuation application of U.S. nonprovisional patent application Ser. No. 13/762,453 filed on Feb. 8, 2013 (now U.S. Pat. No. 8,679,489), which is a continuation application of U.S. nonprovisional patent application Ser. No. 13/224,943 filed on Sep. 2, 2011 (now U.S. Pat. No. 8,388,956), which is a divisional application of U.S. nonprovisional patent application Ser. No. 12/455,458, filed on Jun. 1, 2009 (now U.S. Pat. No. 8,034,337), which claims the priority of U.S. provisional patent applications Ser. Nos. 61/057,586, 61/121,391, and 61/178,350 filed on May 30, 2008, Dec. 10, 2008, and May 14, 2009, respectively; all of which are incorporated herein by reference.

STATEMENT AS TO FEDERALLY SPONSORED RESEARCH

Not applicable.

FIELD OF THE INVENTION

The invention relates generally to the fields of immunology, inflammation, cancer, vascular disorders, and medicine. More particularly, the invention relates to antibodies (Abs) which specifically bind interleukin-1α (IL-1α) and methods of using such Abs to treat, prevent, or detect a pathology associated with aberrant IL-1α expression.

BACKGROUND

IL-1α is pro-inflammatory cytokine that plays a role in a number of different activities including inflammation, immune responses, tumor metastasis, and hematopoiesis. IgG autoantibodies against IL-1α occur naturally in the general human population and are thought to be beneficial in diseases such as atherosclerosis.

SUMMARY

The invention is based on the development of fully human monoclonal Abs (mAbs) that include (i) an antigen-binding variable region that exhibits very high binding affinity for human IL-1α and (ii) a constant region that is effective at both activating the complement system though C1q binding and binding to several different Fc receptors. The IL-1α specific mAbs described herein was made by replacing the constant region of a human IgG4 mAb having a variable region specific for human IL-1α with the constant region of a human IgG1 mAb.

Accordingly, the invention features a purified human IgG1 mAb that specifically binds to human IL-1α, the mAb including a heavy chain covalently joined to a light chain. The heavy chain can include the amino acid sequence of SEQ ID NO: 9 and the light chain can include the amino acid sequence of SEQ ID NO:11.

Also within the invention is a set of isolated nucleic acids including a first nucleic acid encoding the heavy chain of a human IgG1 mAb that specifically binds to IL-1α, and a second nucleic acid encoding the light chain of the human IgG1 mAb that specifically binds to human IL-1α. The first nucleic acid can encode the amino acid sequence of SEQ ID NO: 9 and the second nucleic acid can encode the amino acid sequence of SEQ ID NO:11. The first nucleic acid can include the nucleotide sequence of SEQ ID NO: 10 and the second nucleic acid can include the nucleotide sequence of SEQ ID NO:12.

In another aspect, the invention features an expression vector including a nucleic acid encoding the amino acid sequence of SEQ ID NO: 9 or SEQ ID NO: 11.

Another feature of the invention is an isolated host cell (e.g. a mammalian cell such as a CHO cell) including set of isolated nucleic acids including a first nucleic acid encoding the heavy chain of a human IgG1 mAb that specifically binds to IL-1α, and a second nucleic acid encoding the light chain of the human IgG1 mAb that specifically binds to human IL-1α. The heavy chain can include the amino acid sequence of SEQ ID NO: 9 and a light chain can include the amino acid sequence of SEQ ID NO:11.

The invention further features a method of killing a cell expressing human IL-1α. This method can include the step of contacting the cell with a purified human IgG1 mAb that specifically binds to human IL-1α.

A method of inhibiting migration of a human cell through a basement membrane matrix is also within the invention. This method can include the step of adding a purified mAb that specifically binds to human IL-1α to a mixture including a basement membrane matrix and the human cell.

Further within the invention is a method of inhibiting an IL-1α-induced increase in ICAM-1 and/or E-selectin expression on the surface of a human endothelial cell. This method can include the step of adding a purified mAb that specifically binds to human IL-1α to a mixture including the endothelial cell and IL-1α.

The invention additionally includes a method of tracking inflammation in a human subject previously subjected to the steps of: obtaining from the subject a first sample of peripheral blood mononuclear cells at a first time; contacting the first sample with a purified mAb that specifically binds to human IL-1α; and determining the percent of cells in the first sample that bind the monoclonal Ab. This method can include the steps of: (a) obtaining from the subject a second sample of peripheral blood mononuclear cells at a second time; (b) contacting the second sample with the purified mAb that specifically binds to human IL-1α; (c) determining the percent of cells in the second sample that bind the monoclonal Ab; and (d) comparing the percent of cells in the first sample that bind the mAb to the percent of cells in the second sample that bind the monoclonal Ab.

In the foregoing methods, the purified mAb can be a human IgG1 mAb including a heavy chain covalently joined to a light chain, e.g., wherein the heavy chain includes the amino acid sequence of SEQ ID NO: 9 and the light chain includes the amino acid sequence of SEQ ID NO:11.

Another method within the invention features the steps of: (a) enriching a biological sample obtained from a human subject using a filter to separate molecules according to molecular weight into a first fraction including intact IgG complexed with IL-1α and second fraction including molecules less than 100 Kda; and (b) quantifying the amount of IL-1α in the first fraction.

Yet another method within the invention features the steps of: (a) enriching a sample of plasma obtained from a human subject using a filter that separates molecules according to molecular weight into a first fraction including intact IgG complexed with IL-1α and second fraction including molecule less than 100 Kda; (b) adding the first fraction to a substrate including immobilized anti-human IgG Abs under conditions that allow IgG in the first fraction to specifically bind the anti-human IgG Abs immobilized on the substrate; (c) washing the substrate to remove material in the first fraction that does not specifically bind the immobilized anti-human IgG Abs; (d) contacting the substrate washed in step (c) with an Ab that specifically binds human IL-1α under conditions that allows the Ab that specifically binds human IL-1α to specifically bind any human IL-1α bound to the substrate; (e) washing the substrate to remove any of the Ab that specifically binds human IL-1α that is not bound to the substrate; and (f) quantifying the amount of Ab that specifically binds human IL-1α remaining bound to the substrate after step (e).

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994.

The term "specifically binds", as used herein, when referring to a polypeptide (including Abs) or receptor, refers to a binding reaction which is determinative of the presence of the protein or polypeptide or receptor in a heterogeneous population of proteins and other biologics. Thus, under designated conditions (e.g. immunoassay conditions in the case of an Ab), the specified ligand or Ab binds to its particular "target" and does not bind in a significant amount to other proteins present in the sample or to other proteins to which the ligand or Ab may come in contact in an organism. Generally, a first molecule that "specifically binds" a second molecule has an equilibrium affinity constant greater than about $10^5$ (e.g., $10^6$, $10^7$, $10^8$, $10^9$, $10^{10}$, $10^{11}$, and $10^{12}$ or more) liters/mole for that second molecule.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

Although methods and materials similar or equivalent to those described herein can be used in the practice or testing of the present invention, suitable methods and materials are described below. All applications and publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses compositions and methods relating to fully human mAbs that include (i) an antigen-binding variable region that exhibits very high binding affinity for IL-1α and (ii) a constant region that is effective at both activating the complement system though C1q binding and binding to several different Fc receptors. The below described preferred embodiments illustrate adaptation of these compositions and methods. Nonetheless, from the description of these embodiments, other aspects of the invention can be made and/or practiced based on the description provided below.

Methods involving conventional immunological and molecular biological techniques are described herein. Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. Cell culture techniques are generally known in the art and are described in detail in methodology treatises such as Culture of Animal Cells: A Manual of Basic Technique, 4th edition, by R Ian Freshney, Wiley-Liss, Hoboken, N.J., 2000; and General Techniques of Cell Culture, by Maureen A Harrison and Ian F Rae, Cambridge University Press, Cambridge, UK, 1994. Methods of protein purification are discussed in Guide to Protein Purification: Methods in Enzymology, Vol. 182, Deutscher M P, ed., Academic Press, San Diego, Calif., 1990.

In one aspect, the invention features a fully human mAb that includes (i) an antigen-binding variable region that exhibits very high binding affinity for human IL-1α and (ii) a constant region that is effective at both activating the complement system though C1q binding and binding to several different Fc receptors. The human Ab is preferably an IgG1. The Ka of the Ab is preferably at least $1 \times 10^9$ M$^{-1}$ or greater (e.g., greater than $9 \times 10^{10}$ M$^{-1}$, $8 \times 10^{10}$ M$^{-1}$, $7 \times 10^{10}$ M$^{-1}$, $6 \times 10^{10}$ M$^{-1}$, $5 \times 10^{10}$ M$^{-1}$, $4 \times 10^{10}$ M$^{-1}$, $3 \times 10^{10}$ M$^{-1}$, $2 \times 10^{10}$ M$^{-1}$, or $1 \times 10^{10}$ M$^{-1}$).

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects (e.g., subjects not previously administered a human IL-1α vaccine) are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α- specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, Monoclonal Abs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899, now U.S. Pat. No. 8,524,865. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and *E. coli* cells). Because Igs include heavy (H) and light (L) chains in an $H_2L_2$ configuration, the genes encoding each may be separately isolated and expressed in different vectors.

Although generally less preferred, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. E. G., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, monoclonal Abs with a desired binding specificity can be commercially humanized or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs. In addition to human IL-1α mAbs, the Ab compositions of the invention might also include other mAbs that specifically bind antigens other than human IL-1α.

To modify or enhance their function, the human IL-1α mAbs might be conjugated another molecule such as a cytotoxin or detectable label. A human IL-1c specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}$S, $^{14}$C, $^{32}$P, $^{125}$I, $^{131}$I, $^{90}$Y, $^{89}$Zr, $^{201}$Tl, $^{186}$Re, $^{188}$Re, $^{57}$Cu, $^{213}$Bi, and $^{211}$At), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), *Pseudomonas* exotoxin (PE) A, PE40, abrin, saporin, pokeweed viral protein, ethidium bromide, glucocorticoid, anthrax toxin and others. See, e.g., U.S. Pat. No. 5,932,188.

The human IL-1α specific mAb can also be conjugated to a detectable label. Useful detectable labels in the present invention include biotin or streptavidin, magnetic beads, fluorescent dyes (e.g., fluorescein isothiocyanate, texas red, rhodamine, green fluorescent protein, and the like), radiolabels (e.g., $^3$H, $^{125}$I, $^{35}$S, $^{14}$C, $^{32}$P, $^{111}$In, $^{97}$Ru, $^{67}$Ga, $^{68}$Ga, or $^{72}$As), radioopaque substances such as metals for radioimaging, paramagnetic agents for magnetic resonance imaging, enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters. Fluorescent markers may also be used and can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The present invention also encompasses nucleic acid molecules encoding fully human mAbs specific for human IL-1α. Although the same nucleic acid molecule might encode both the heavy and light chains of a human IL-1α-specific mAb, two different nucleic acid molecules, one encoding the heavy chain and the other encoding the light chain might also be used. The amino acid sequences of three IgG1 mAbs specific for human IL-1α are presented herein. See SEQ ID NOs: 1, 3, 5, 7, 9, and 11. Exemplary nucleic acid molecules encoding these amino acid sequences are also described herein. See SEQ ID NOs: 2, 4, 6, 8, 10, and 12. Any other suitable nucleic acid that encodes the amino acid sequences of the two described IgG1 mAbs or other mAbs within the invention might also be used.

For production of mAbs, the nucleic acid molecules of the invention might be incorporated into an expression vector in an orientation wherein such nucleic acid molecules are operatively linked to expression control sequences such as transcriptional and translational control sequences. Examples of expression vectors include vectors derived from plasmids and vectors derived from viruses such as adenoviruses, adeno-associated viruses, and retroviruses. The nucleic acid molecules encoding a light chain and a heavy chain might be incorporated into a single vector or different vectors. The vectors of the invention might also include regulatory sequences such as promoters and/or enhancers (see, U.S. Pat. Nos. 5,168,062, 4,510,245 and 4,968,615), selectable markers, or sequences encoding affinity tags (for facilitating purification) or a detectable label.

For production of mAbs, the vectors of the invention can be introduced into a suitable host cell, e.g., a prokaryotic cell such as a bacteria or, preferably, a eukaryotic cell such as mammalian, plant, or yeast host cell. Examples of methods for introducing heterologous polynucleotides into host cells include use of viral vectors, electroporation, encapsulation of the polynucleotide(s) in liposomes, dextran-mediated transfection, calcium phosphate precipitation, polybrene-mediated transfection, protoplast fusion, *Agrobacterium*-mediated transformation, biolistic transformation, and direct microinjection of the DNA into nuclei. Mammalian cell lines are presently preferred for expression of mAbs from vectors. Examples of mammalian host cells include Chinese hamster ovary (CHO) cells (e.g., the DG44 CHO cell line), HeLa cells, baby hamster kidney (BHK) cells, African green monkey kidney cells (COS), human hepatocellular carcinoma cells (e.g., Hep G2), NS0 cells, SP2 cells, HEK-293T cells, 293 Freestyle cells, and NIH-3T3 cells. The mAbs of the invention might also be expressed in transgenic animals or plants. See, e.g., U.S. Pat. Nos. 5,827,690; 5,756,687; 5,750,172; 5,741,957; 6,046,037; and 5,959,177.

The invention provides a method for detecting a human IL-1α-expressing cell in a sample by contacting the cell with a human IL-1α-specific mAb and detecting the mAb bound to the cell. The invention also provides a method for killing a human IL-1α-expressing cell by contacting the cell with a human IL-1α-specific mAb. Such killing can be accomplished by complement-mediated killing, Ab-dependent cell-mediated cytotoxicity, or Ab-mediated delivery of a cytotoxin. The Abs described herein have also been shown to be useful for other methods.

For example, MABp1 has been to reduce IL-1α induced ICAM1 and E-selectin expression on endothelial cells. MABp1 has also been shown to be used in immunoassays for detecting and quantifying IL-1α in a biological sample.

EXAMPLES

Example 1—Cloning of Anti-hIL-1α IgG1 and Kappa Chains

Variable region heavy chain (V-HC) and variable region light chain (V-LC) sequences were gene synthesized using amino acid sequence information provided in U.S. Pat. No. 5,959,085. V-HC was PCR amplified introducing HindIII/ClaI sites upstream of the ATG start codon and a NheI site at the 3' end. The human germline IgG1 constant region (including exons and introns) was PCR amplified modifying the two 5' triplets encoding for the first two amino acids Ala-Ser to an NheI site, and introducing a BamHI site at the 3' end. The human germline IgG1 constant region amino acid sequence corresponded to Swiss-Prot entry P01857, except for a K171Q and a V261L exchange. The V-HC and constant IgG1-HC sequence were ligated using the NheI site and cloned into pcDNA3 using HindIII and BamHI sites.

```
>hIL-1a-IgG1-HC
                                          (SEQ ID NO: 1)
MEFGLSWVFLVALLRGVQCQVQLVESGGGVVQPGRSLRLSCTASGFTFSM

FGVHWVRQAPGKGLEWVAAVSYDGSNKYYAESVKGRFTISRDNSKNILFL

QMDSLRLEDTAVYYCARGRPKVVIPAPLAHWGQGTLVTFSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAQTKPREEQYNSTYRVVSVLTVLHQDWLNGKEYKCKVSNK

ALPAPIEKTISKAKGQPREPQVYTLPPSRDELTKNQVSLTCLVKGFYPSD

IALEWESNGQPENNYKTTPPVLDSDGSFFLYSKLTVDKSRWQQGNVFSCS

VMHEALHNHYTQKSLSLSPGK

>hIL-1a-IgG1-HC
                                          (SEQ ID NO: 2)
atggagttcgggctgagttgggtgttcctggtggctctgctgcggggcgt gcagtgccaggtgcagctggtggagagtggggggtggcgtggtgcagcctg gccggtctctgcgcctgtcttgcactgcctccggattacchttctatght ggtgtgcactgggtgcgccaggctcccggcaagggactggaatgggtggc cgccgtgagttacgacgggtccaacaaatattacgctgagagcgtgaaag gcagattcaccatcagcagagataattccaagaatattctgttcctgcag atggacagtctgagactggaggacactgctgtgtactactgcgctcgtgg acgccctaaggtggtcatcccgcccctggcacattggggccagggaa ctctggtgaccttactagcgctagcaccaagggcccatcggtatccct ggcaccctcctccaagagcacctctgggggcacagcggccctgggctgcc tggtcaaggactacttccccgaaccggtgacggtgtcgtggaactcaggc gccctgaccagcggcgtccacaccttcccggctgtcctacagtcctcagg actctactccctcagcagcgtagtgaccgtgccctccagcagcttgggca cccagacctacatctgcaacgtgaatcacaagcccagcaacaccaaggtg gacaagaaagttgagcccaaatcgtgacaaaactcacacatgcccaccg tgcccagcacctgaactcctggggggaccgtcagtchcctcacccccaa
```

-continued
aacccaaggacaccctcatgatctcccggacccctgaggtcacatgcgtg gtggtggacgtgagccacgaagaccctgaggtcaagttcaactggtacgt ggacggcgtggaggtgcataatgcccagacaaagccgcgggaggagcagt acaacagcacgtaccgtgtggtcagcgtcctcaccgtcctgcaccaggac tggctgaatggcaaggagtacaagtgcaaggtctccaacaaagccctccc agccccatcgagaaaaccatctccaaagccaaagggcagccccgagaac cacaggtgtacaccctgcccccatcccgggatgagctgaccaagaaccag gtcagcctgacctgcctggtcaaaggcttctatcccagcgacatcgccct ggagtgggagagcaatgggcagccggagaacaactacaagaccacgcctc ccgtgctggactccgacggctccttcttcctctacagcaagctcaccgtg gacaagagcaggtggcagcaggggaacgtcttctcatgctccgtgatgca tgaggctctgcacaaccactacacgcagaagagcctctccttaagtccgg gaaaataa The V-LC was PCR amplified introducing HindIII/ClaI sites upstream of the ATG start codon and a BsiWI site at the 3' end. The human constant Kappa-LC sequence was PCR amplified introducing a 5' BsiWI site encoding an additional Arg and the first amino acids Thr, and a BamHI site at the 3' end. The human constant Kappa-LC amino acid sequence corresponded to Swiss-Prot entry P01834. V-HC and constant Kappa-LC sequences were ligated using the BsiWI site and cloned into pcDNA3 using HindIII and BamHI sites.

>hIL-1a-K-LC
[SEQ ID NO: 3]
MDMRVPAQLLGLLLLWFPGSRCDIQMTQSPSSVSASVGDRVTITCRASQG

ISSWLAWYQQKPGKAPKLLIYEASNLETGVPSRFSGSGSGSDFTLTISSL

QPEDFATYYCQQTSSFLLSFGGGTKVEHRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

>hIL-1a-K-LC
[SEQ ID NO: 4]
atggacatgcgcgtgcccgcccagctgctggggctgctgctgctgtggtt ccctggatctaggtgcgacattcagatgacccagtcccccagctcagtgt cagcctccgtgggcgacagagtgacaatcacctgccgcgcctctcaggga atctctagttggctggcctggtaccagcagaagcctggaaaggcccccaa gctgctgatctatgaagcctccaacctggagaccggcgtgccctctcgct tcagcggctcaggctcaggcagtgatatactctgaccatcagctccctgc agccagaggatttcgctacttactactgccagcagaccthccacctgct gtccttcggggaggcacaaggtggagcaccgtacggtggctgcaccat ctgtcttcatcaccgccatctgatgagcagttgaaatctggaactgcct ctgttgtgtgcctgctgaataacttctatcccagagaggccaaagtacag tggaaggtggataacgccctccaatcgggtaactcccaggagagtgtcac agagcaggacagcaaggacagcaccctacagcctcagcagcaccctgacgc tgagcaaagcagactacgagaaacacaaagtctacgcctgcgaagtcacc catcagggcctgagttcaccggtgacaaagagcttcaacaggggagagtg ttag

Example 2—Generation of NATHMAB-hIL-1α IgG1 and Kappa Chain

The complete sequence encoding the NATHMAB-hIL-1a/IgG1 heavy chain was gene synthesized. The V-HC sequence corresponded to the amino acid sequence described in U.S. Pat. No. 5,959,085. The human constant IgG1-HC sequence corresponded to Swiss-Prot entry P01857. The nucleotide sequence was codon optimized for expression in CHO cells. A Kozac sequence (gccacc) was added upstream of the start ATG.

>NATHMAB-hIL-1A-IGG1-HC
[SEQ ID NO: 5]
MEFGLSWVFLVALLRGVQCQVQLVESGGGVVQPGRSLRLSCTASGFTFSM

FGVHWVRQAPGKGLEWVAAVSYDGSNKYYAESVKGRFTISRDNSKNILFL

QMDSLRLEDTAVYYCARGRPKVVIPAPLAHWGQGTLVTFSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK

>NATHMAB-hIL-1A-IGG1-HC
[SEQ ID NO: 6]
gccaccatggagtttggtctgtcctgggtgttcttggtggctctgctgag ggggtgcagtgccaggtccagctggtggagtctggtggggagtggtgc agcctgggagatctctgcggctgtcttgcactgcctctggtttcactttc tctatgtttggtgtgcaagggtcaggcaagcaccaggcaaaggactcgag tgggtcgcagctgtgagctatgacgggtctaacaaatattacgctgagtc tgtcaagggtaggataccatcagccgggataattccaaaaatatcctgac ctgcaaatggactctctgaggctggaagatactgcagtctactattgtgc aaggggggaggccaaaggtggtgatccccgctcccctcgctcactggggac agggaaccctggtgactacagctctgctagcaccaagggccctagcgtga cccattggctccacctccaaatctacttctggaggcaccgccgccctggg atgtctcgtgaaagattattttcctgagcccgtcaccgtgagctggaaca gcggcgccctgactagcggcgtgcacaccatcccgcagtgctgcaatcta gcgggctgtactccctgagctctgtcgtgaccgtgccctccagcagcctc ggaactcagacctacatctgcaatgtcaatcataaaccctctaataccaa agtcgataagaaggtcgaacctaaatcagcgataaaaccatacctgccc cccttgcccagcaccgaactgctgggcggtccctctgtgatctgacccc cccaaacccaaagatacctgatgatctctaggaccccgaggtcacttg -continued

```
tgtcgtggtggatgtgtcccacgaagatccagaagtcaaattcaactggt atgtggacggggtcgaagtgcacaacgcaaagaccaagcctagggaggaa cagtataatagcacatatagggtggtcagcgtcctgaccgtcctgcatca ggactggctgaatggcaaagaatataagtgtaaagtgtccaacaaggccc tgccagccccaatcgaaaagacaatctctaaagcaaggggcaacccgg gaacctcaggtctatacactgccaccctctcgggatgaactgaccaagaa tcaggtgagcctgacatgtcagtgaagggtattatccctccgacattgcc gtggagtgggagagcaatggacaaccagaaaataactacaaaaccacacc ccctgtgctggactccgatggaccacttcctctactctaagctgacagtg gataagtctaggtggcagcaggggaatgtgactcctgctctgtgatgcac gaggcactgcacaatcattatacacaaaagtctctgtctctgtctccagg aaagtaa
```

The complete sequence encoding the NATHMAB-hIL-1a/Kappa light chain was gene synthesized. The V-LC sequence corresponded to the amino acid sequence described in U.S. Pat. No. 5,959,085. The human constant Kappa-LC sequence corresponded to Swiss-Prot entry P01834. The nucleotide sequence was codon optimized for expression in CHO cells. A Kozac sequence (gccacc) was added upstream of ATG.

>NATHMAB-hIL-1A-K-LC
[SEQ ID NO: 7]
MDMRVPAQLLGLLLLWFPGSRCDIQMTQSPSSVSASVGDRVTITCRASQG

ISSWLAWYQQKPGKAPKLLIYEASNLETGVPSRFSGSGSGSDFTLTISSL

QPEDFATYYCQQTSSFLLSFGGGTKVEHTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

NATHMAB-hIL-1A-K-LC
[SEQ ID NO: 8]
```
gccaccatggacatgcgcgttcctgcccagctcctcggactgctgctgct ttggttcccaggctcccggtgtgatattcagatgacacagtctccctcct ccgtatctgcatccgtgggcgacagggtcacaatcacttgtagggccagc caggggatctctagttggctcgcatggtaccaacaaaagccaggtaaggc tccgaaactgctcatttacgaagctagtaacctcgaaacaggcgtgccaa gccggtttagcggctccggttccggttctgacttcaccctcactatttcc tccctgcaacctgaggattttgccacatattactgtcagcaaacttcttc ttttctgctctcctttggtgggggaactaaggtggagcacacagtggccg cccccagcgtctttatcttcccccaagcgatgaacagctgaagtcaggg accgccagcgtggtctgcctgctcaataattttaccctcgcgaggctaa ggtccaatggaaagtggataacgccctccagagcggtaactctcaggagt ctgtcacagagcaagacagcaaggatagcacctattccctctccagcacc ctgacactgtctaaggccgactacgagaaacacaaagtgtacgcttgtga ggtgactcaccagggactgagtagccctgtgacaaaatctttcaataggg gagaatgctga
```

Example 3—Expression of NATHMAB-IL1-a (IgG1/k Subtype)

NATHMAB-IL-1α was expressed and purified using a transient transfection method. Cell culture supernatant or protein G affinity purified Ab was subjected to further analysis as described below. Human embryonic kidney (HEK) 293T cells were cultured in DMEM containing 10% FCS, and transiently transfected using jetPEI reagent (Polyplus) according to manufacturer's protocol. Cells were seeded on 10 cm dishes (3×10⁶ cells per 10 cm dish) 24 h prior to transfection to reach approximately 50% density at the time point of transfection. 5 μg per dish of pcDNA3-anti-hIL-1α-IgG1-HC and a 2-fold molar excess of pcDNA3-anti-hIL-1α-Kappa were used for transfection. After recovery, medium was changed to DMEM containing 2% FCS (10 ml per dish) and Ab was collected for 5 to 6 days. The supernatant was collected, filtered, pH adjusted to 7.5-8, and stored at 4° C. until further use.

Part of the supernatant (250 ml) was incubated with protein G sepharose (GE Healthcare) for 3 h at 4° C. on a rotation wheel. Then, the protein G sepharose was loaded onto a gravity flow column and washed with PBS. Ab was eluted in 1 ml fractions using 100 mM glycine/150 mM NaCl into 100 μl Tris (pH 8), followed by dialysis with PBS containing 10% glycerol. The total protein concentration of each fraction was measured using the BCA Protein Detection Kit (Pierce). Correct size of heavy and light chains, and of the assembled native Ab was confirmed by SD S-PAGE.

Supernatant containing NATHMAB-hIL-1α purified Ab and Triton X-100 cell lysates of producer HEK 293T cells were tested for antigen binding in a radioimmunoassay (RIA) using $^{125}$I-hIL-1α. Binding was assayed by absorption to protein G. All samples bound $^{125}$I-hIL-1α with highest activity in the eluate. Binding of purified NATHMAB-hIL-1α in a concentration of 0.012% (half-max activity in RIA) to $^{125}$I-hIL-1α was used for measuring the affinity coefficient. The Ka of NATHMAB-hIL-1α under these conditions was $3.03 \times 10^{10}$ M$^{-1}$. Back calculation revealed an estimated concentration of approximately 30 μg/ml active anti-hIL-1α-IgG in the purified eluate.

Neutralizing activity of NATHMAB-hIL1α was tested in a bioassay using the murine EL4-6.1 subline which produces high levels of IL-2 when treated with murine or human IL-1α (Zubler et al., J. Immunol. 134:3662-3668, 1985). The indicated concentrations of NATHMAB-hIL-1α (eluate) were incubated for 30 min at 37° C. with various concentrations of recombinant hIL-1α (eBioscience) in a final volume of 100 μl/well in a 96-well culture plate (flat bottomed). Each point was carried out in triplicate and in culture medium (DMEM, 5% FCS). To each well were added 100 μl of a suspension of EL4-6.1 cells (5×10⁵ cells/ml) in culture medium containing 0.2 μg/ml ionomycin. After incubation for 24 h at 37° C. in a 5% CO₂ incubator, cell free supernatants were harvested and assayed for IL-2 concentrations using a commercially available ELISA (R&D Systems). The results showed that NATHMAB-IL-1α effectively neutralized hIL-1α-induced IL-2 secretion by EL-4 cells.

To test for neutralization of membrane-bound hIL-1α, the same EL-4 cell-based assay as described above was used with following modifications. Different concentrations of NATHMAB-hIL-1α (eluate) were incubated with various numbers of human activated monocytes. For monocyte preparation, PBMC were isolated from buffy coat using Ficoll-Paque centrifugation. Monocytes were allowed to adhere for 1.5 h at 37° C. in RPMI on plastic dishes.

Non-adherent lymphocytes were washed away to yield a nearly pure monocyte culture. Monocytes were cultured in RPMI containing Gln, Pyr, and 10% FCS for 24 h with LPS (1 µg/ml) at 37° C. in a 5% $CO_2$ incubator. Cells were detached with PBS/2 mM ED TA, carefully scraped from plates, and transferred into Falcon tubes. Cells were washed twice with PBS, resuspended in PBS/1% PFA and fixed for 10 min at 20° C. Cells were washed with glycine buffer (150 mM glycine, 75 mM NaCl, pH 7.4), then with culture medium and counted. The results showed that NATHMAB-hIL-1α effectively neutralized IL-2 secretion by EL-4 cells induced by membrane-bound hIL-1α. In an experiment similar to that described above, NATHMAB-hIL-1α was tested for neutralization of murine IL-1α. Indicated amounts of NATHMAB-hIL-1α supernatant were incubated with recombinant human (h) or murine (m) IL-1α (eBioscience). The supernatant containing the Ab neutralized human, but not murine, IL-1α.

Example 4—Ab-Mediated Killing of Cancer Cells

Human peripheral blood mononuclear cells (PBMC) isolated from the buffy coat by standard Ficoll Paque preparation were incubated in either RPMI-1640 CM or RPMI-1640-CM containing rhIL-2 (30 ng/ml, ebioscience) at 37° C. and 5% CO2 overnight and used as effector cells (E). THP1 cells were used as the targets (T). The assay was carried out in 96-well plates with each point in triplicate. After $1 \times 10^4$ targets that were incubated with different concentration of MABp1 for 15 mins, effector cells were added in an ET ratio of 25:1 and 50:1 to $1 \times 10^4$ targets and incubated for another 4 hours. 75 ul of assay volume were transferred to a new 96-well plate and cytotoxicity was assayed using the LDH cytotoxicity detection kit (Roche) according to manufacturer's protocol. % specific lysis= (mean experimental release-mean spontaneous release without antibody)×100/(mean maximal release from targets-mean spontaneous release from targets) A. untreated PBMC were used as effector cells. B. rhIL-2-treated PBMC were used as effector cells. In both cases, increasing concentrations (1.25 to 20 ug/ml) of MABp1 resulted in increased target cell killing (up to about 90%) at both ET ratios.

Example 5—Human Anti-IL1α Specific mAb Sequences

The complete sequence encoding for another human anti-hIL-1αIgG$_1$/Kappa light chain specific for human IL1α (MABp1) was synthesized and expressed as described above. In the nucleic acids encoding the heavy and light chains, a Kozac sequence (gccacc) was added upstream of the start ATG.

Heavy Chain
[SEQ ID NO: 9]
MEFGLSWVFLVALLRGVQCQVQLVESGGGVVQPGRSLRLSCTASGFTFSM

FGVHWVRQAPGKGLEWVAAVSYDGSNKYYAESVKGRFTISRDNSKNILFL

QMDSLRLEDTAVYYCARGRPKVVIPAPLAHWGQGTLVTFSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

[SEQ ID NO: 10]
gccaccatggagtttggtctgtcctgggtgttcttggtggctctgctgag gggggtgcagtgccaggtccagctggtggagtctggtgggggagtggtgc agcctgggagatctctgcggctgtcttgcactgcctctggtttcactttc tctatgtttggtgtgcaagggtcaggcaagcaccaggcaaaggactcgag tgggtcgcagctgtgagctatgacgggtctaacaaatattacgctgagtc tgtcaagggtaggataccatcagccgggataattccaaaaatatcctgac ctgcaaatggactctctgaggctggaagatactgcagtctactattgtgc aaggggaggccaaaggtggtgatccccgctccctcgctcactggggac agggaaccctggtgactacagctctgctagcaccaagggccctagcgtga cccattggctccacctccaaatctacttctggaggcaccgccgccctggg atgtctcgtgaaagattattttcctgagcccgtcaccgtgagctggaaca gcggcgccctgactagcggcgtgcacaccatcccgcagtgctgcaatcta gcgggctgtactccctgagctctgtcgtgaccgtgccctccagcagcctc ggaactcagacctacatctgcaatgtcaatcataaaccctctaataccaa agtcgataagagggtcgaacctaaatcagcgataaaacccatacctgccc cccttgcccagcacccgaactgctgggcggtccctctgtgatctgacccc cccaaacccaaagatacctgatgatctctaggaccccgaggtcacttg tgtcgtggtggatgtgtcccacgaagatccagaagtcaaattcaactggt atgtggacggggtcgaagtgcacaacgcaaagaccaagcctagggaggaa cagtataatagcacatatagggtggtcagcgtcctgaccgtcctgcatca ggactggctgaatggcaaagaatataagtgtaaagtgtccaacaaggccc tgccagccccaatcgaaaagacaatctctaaagccaaggggcaaccccgg gaacctcaggtctatacactgccaccctctcgggaggaaatgaccaagaa tcaggtgagcctgacatgtcagtgaagggtattatccctccgacattgcc gtggagtgggagagcaatggacaaccagaaaataactacaaaaccacacc ccctgtgctggactccgatggaccacttcctctactctaagctgacagtg gataagtctaggtggcagcaggggaatgtgactcctgctctgtgatgcac gaggcactgcacaatcattatacacaaaagtctctgtctctgtctccagg aaagtaa Light Chain
[SEQ ID NO: 11]
MDMRVPAQLLGLLLLWFPGSRCDIQMTQSPSSVSASVGDRVTITCRASQG

ISSWLAWYQQKPGKAPKLLIYEASNLETGVPSRFSGSGSGSDFTLTISSL

QPEDFATYYCQQTSSFLLSFGGGTKVEHKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC

-continued

[SEQ ID NO: 12]
```
gccaccatggacatgcgcgttcctgcccagctcctcggactgctgctgct ttggttcccaggctcccggtgtgatattcagatgacacagtctccctcct ccgtatctgcatccgtgggcgacagggtcacaatcacttgtagggccagc caggggatctctagaggctcgcatggtaccaacaaaagccaggtaaggct ccgaaactgctcatttacgaagctagtaacctcgaaacaggcgtgccaag ccggatagcggctccggaccggactgacttcaccctcactatacctccct gcaacctgaggattagccacatattactgtcagcaaacttatcattctgc tctcctaggtggaggaactaaggtggagcacaagcggacagagctgctcc tagcgtattatcaccctccaagcgatgaacagctgaagtcagggaccgcc agcgtggtctgcctgctcaataattatccctcgcgaggctaaggtccaa tggaaagtggataacgccctccagagcggtaactctcaggagtctgtcac agagcaagacagcaaggatagcacctattccctctccagcaccctgacac tgtctaaggccgactacgagaaacacaaagtgtacgcagtgaggtgactc accagggactgagtagccctgtgacaaaatctttcaataggggagaatgc tga
```

Example 6—MABp1 Binding Affinity

The binding affinity of purified MABp1 was determined using surface plasmon resonanace (SPR) on a BIAcore 2000 instrument (GE Health Sciences). A mouse monoclonal anti-human IgG (Fc) Ab was covalently immobilized on the flow cells of a CMS sensor chip using a human Ab capture kit and amine coupling kit (GE Health Sciences). Immobilization levels of 8000-14000 RU would typically be achieved. After immobilization of the mouse anti-human IgG (Fc) capture Ab, three start-up cycles with HBS-EP running buffer (GE Health Sciences) and two start-up cycles with MABp1 were run to stabilize the CMS surface and to remove any non-covalently bound Ab. For analysis, MABp1 Ab was diluted into HBS-EP running buffer to a final concentration of 1 µg/mL and immobilized to 700 RU on one flow cell of the CMS sensor chip. Carrier-free human IL-1A cytokine (eBioscience, #34-8019) was serially diluted in HBS-EP running buffer over a test range from 100 nM to 0.05 nM. Flow rate was 30 µl/min. Dissociation data for each cytokine dilution was recorded for 15 minutes. The CMS surface was regenerated after each cycle using a single injection of 3 M $MgCl_2$ for 25 seconds at a flow rate of 30 µl/min. BiaEvaluation software and a Langmuir binding model was used to fit the data. The $K_D$ for MABp1 was determined to be less than $2.0 \times 10^{-10}$ M.

Example 7—MABp1 Inhibits Tumor Cell Invasion of a Basement Membrane Matrix

Matrigel (BD), a basement membrane matrix, was thawed at 4° C. overnight and the dilute (5 mg/ml to 1 mg/ml) in serum free cold cell culture media. 100 ul of the diluted matrigel was placed into the upper chambers of a 24-well transwell (Costar) and the transwell was incubated at 37° C. for at least 4 to 5 h for gelling. Tumor cells (MDA-MB-231 and THP-1) were harvested from tissue culture flasks by Trypsin/EDTA, washed with culture media, and resuspended in medium containing 1% FBS at a density of $1 \times 10^6$ cells/ml. The gelled matrigel was gently washed with warmed serum free-culture media, and 100 ul of the cell suspension was added in each well. The lower chamber of the transwell was filled with 600 ul of culture media, and the plates was incubated at 37° C. for 12 to 24 h. The cells that did not invade the matrigel were gently scraped off the top of each transwell with a cotton swab. The transwells were then removed from the 24-well plates and stained with crystal violet after fixing the invaded cells with 70% ethanol or methanol. The invaded cells were counted under a light microscope. The percent of cells invading the matrigel was significantly inhibited in the presence of MABp1.

Example 8—MABp1 Blocks Increase in ICAM1 Expression in Endothelial Cells

Human umbilical vein endothelial cells (HUVEC) (BD Biosciences) were seeded to 24-well plates at $5 \times 10^5$ per well in 1 mL of M-200 medium supplemented with low-serum growth supplement (Invitrogen). Cells were allowed to settle for 3-4 hours. Medium was aspirated and a fresh 1 mL of M-200 was added per well. MABp1 was added directly to cells @ 4.26 µg/mL, co-incubated for 15 minutes at room temperature, and then recombinant human IL-1α (rhIL1A, eBioscience) was added to a final concentration of 40 pg/mL. Positive control wells received the addition of IL-1α only. HUVEC cells in the absence of IL-1α or the absence of MABp1 served as negative controls. After 17-20 hours incubation at 37° C., 5% $CO_2$, cells were lifted from the plates by a non-enzymatic treatment for 20 minutes using CellStripper reagent (Cellgro Mediatech) and then immediately assayed for CD54 (ICAM-1) expression using standard flow cytometry protocols. Staining buffer comprised Dulbecco's PBS supplemented with 2% heat-inactivated fetal bovine serum. PE-conjugated mouse anti-human CD54 (ICAM-1) mAb (eBioscience, clone HA58) or a PE-conjugated mouse IgG1k isotype control (eBioscience, #12-4714) were used per manufacturer's instructions to stain HUVEC cells in a 100 microliter staining volume for 20 minutes in the dark at room temperature. Two washes in staining buffer were subsequently performed and then samples were acquired on a FACSCalibur flow cytometer (BD Biosciences). Among several independent experiments (n=5) the upregulation of ICAM-1 adhesion molecules induced by rhIL1A on the surface of HUVEC cells was neutralized by MABp1 to baseline levels exhibited by the unstimulated HUVEC cells.

Example 9—MABp1 Blocks Increase in E-Selectin Expression in Endothelial Cells Similar to its effects on ICAM-1 induction, MABp1-mediated neutralization of induction of CD62E (E-selectin) on HUVEC cells was also observed. This effect was most pronounced when HUVEC cells were stimulated not by soluble rhIL-1a but by membranous IL-1a anchored by glycosyl-phosphatidylinositol to the surface of DG44 CHO cells (GPI-IL1A cells). In this experiment, confluent cultures of HUVEC cells in 6-well plates were co-cultured overnight with $5 \times 10^6$ GPI-IL1A DG44 cells in M-200 medium, either alone, in the presence of 10 µg/mL MABp1, or in the presence of 10 µg/mL D5 isotype control Ab. After 17-20 hours, HUVEC monolayers were washed extensively with Dulbecco's PBS and then lifted by non-enzymatic treatment for 20 minutes with CellStripper reagent (Cellgro Mediatech) and then immediately assayed for CD62E (E-selectin) expression using standard flow-cytometry protocols. Staining buffer comprised Dulbecco's PBS supplemented with 2% heat-inactivated fetal bovine serum. PE-conjugated mouse anti-human CD62E mAb (eBioscience, clone P2H3) or a PE-conjugated mouse IgG1k isotype control (eBioscience, clone P3) were used per manufacturer's instructions to stain HUVEC cells in a 100 microliter staining volume for 20 minutes in the dark at room temperature. Two washes in staining buffer were subsequently performed and then samples were acquired on a FACSCalibur flow cytometer (BD Biosciences). Upregulated E-selectin expression on the surface of HUVEC cells induced by membranous GPI-IL-1a was neutralized by MABp1 to baseline levels exhibited by unstimulated HUVEC cells.

Example 10—MRC-5 Bioassay for MABp1 Potency (Neutralization of rhIL1A)

The MRC-5 cell line, derived from fetal human lung fibroblasts, was obtained from the ATCC collection (CCL-171). The IL-1 neutralizing potency of MABp1 was assayed by measuring IL-1A induced release of IL-6 from MRC-5 cells. MRC-5 cells were seeded at $5 \times 10^3$ per well to a 96-well plate in 100 microliters of DMEM complete medium. Cells were cultured overnight at 37° C. in a humidified 5% $CO_2$ incubator. Confluent MRC-5 cells were subsequently cultured another 24 hours with 20 pg/mL of recombinant human IL-1A (rhIL1A, eBioscience) either alone or in the presence of increasing concentrations of MABp1. Negative control cells were not stimulated with rhIL1A. After the 24 hours, supernatants were collected and assayed for IL-6 release using and IL-6 ELISA kit from eBioscience. The $IC_{50}$, or concentration of MABp1 required to inhibit 50% of the maximal IL-6 release, was in the range of 0.001-0.01 µg/mL.

Example 11—MABp1 Identifies IL-1a+ Cells

One hundred microliters of sodium heparin anti-coagulated whole blood was aliquoted to polystyrene FACS tubes. Samples were incubated at room temperature for 15 minutes with 1 mg of human IgG (protein-A purified) plus 2 ml of heat-inactivated fetal bovine serum to block Fc receptors. Primary Abs were then added to the sample: Either 1 mg of Alexa-488 labeled MABp1, 1 mg of FITC-labeled monoclonal anti-membrane human IL1A Ab (FAB200F, R&D Systems), or 1 mg of a murine isotype control (IC002F, R&D Systems). Primary Abs were incubated with sample for 30 minutes at room temperature in the dark. Sample erythrocytes were then lysed (BD Biosciences PharmLyse solution) at room temperature for 15 minutes, centrifuged at 300×g for 5 minutes, and aspirated. Sample pellets were washed three times with 1 mL Hank's balanced salt solution (HBSS) containing 2% heat-inactivated fetal bovine serum. Sample was resuspended in 0.3 mL HBSS+2% FBS and data was acquired on a FACSCalibur flow cytometer and analyzed using CellQuest software. Flow cytometric analysis of human PBMC using MABp1 showed that only 0.2% of PBMC were positive for IL-1α.

Example 12—MABp1 for Detecting and Tracking Infections and Inflammation

Flow cytometric analysis (as in Example 11) of human PBMC using MABp1 showed a 3.6-fold increase in the percent of PBMC positive for IL-1α$^+$ in a subject with a sub-clinical infection compared to a normal control. Similarly, in a subject with an inflamed wisdom tooth, an increase in the percent of PBMC positive for IL-1α$^+$. A substantial decrease in the number of IL-1α$^+$ PBMC was observed from 14 to 45 days after removal of the wisdom tooth.

Example 13—Immunoassay for Detecting and/or Quantifying IL-1α

In general, very low levels of IL-1α are present in the plasma of human subjects. Because these levels are often beyond the detection threshold of conventional immunoassays, an ELISA with improved sensitivity was developed. In this ELISA, exogenous anti-IL-1α Ab (e.g., MABp1) can be added to a biological sample being tested (e.g., human plasma) under conditions that allow the Ab to bind IL-1α in the sample. Because, it was observed that almost all IL-1α in human plasma samples exists already bound to endogenous anti-IL-1α Ab, the latter step can often be omitted. The sample with IL-1α-Ab complexes is then applied to a filter (Amicon centrifugal device) with a molecular weight cutoff of about 100 kDa to separate the IL-1α-Ab complexes from molecules in the sample less than the molecular weight cutoff. In one experiment, this resulted in a 50-fold concentration. The processed sample (and dilutions thereof) was then added to wells of a microtiter plate coated with an anti-human IgG capture Ab (2 ug/ml mouse anti-human IgG, Fc-specific, Southern Biotech product code #9042-01). After allowing time to bind the IL-1α-Ab complexes in the sample, the wells were washed to remove non-binding material. A labeled anti-human IL-1α secondary Ab was then added to the wells (0.2 ug/ml biotin-conjugated monoclonal mouse anti-human IL-1A Ab, clone CRM6, eBioscience catalog #13-7017). After allowing time to bind the IL-1α in the wells, the plate was washed and the amount of labeled anti-human IL-1α in each well was quantified as an indication of the concentration of IL-1α in the sample being tested.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A monoclonal antibody having a heavy chain comprising the amino acid residues 20-471 of SEQ ID NO: 9 and a light chain comprising the amino acid residues 23-236 of SEQ ID NO: 11.

2. A pharmaceutical composition comprising the monoclonal antibody of claim 1.

3. A method of inhibiting migration of a human cell through a basement membrane matrix in a subject in need thereof, comprising administering to the subject the pharmaceutical composition of claim 2.

4. A host cell expressing the monoclonal antibody of claim 1.

5. A method of killing a cell expressing human IL-1 alpha, comprising contacting the cell with the monoclonal antibody of claim 1.

6. A method of increasing Intercellular Adhesion Molecule 1 (ICAM1) and E-Selectin expression in human endothelial cells, comprising contacting the human endothelial cells with the monoclonal antibody of claim 1.

7. A monoclonal antibody having a heavy chain consisting of the amino acid residues 20-471 of SEQ ID NO: 9 and a light chain consisting of the amino acid residues 23-236 of SEQ ID NO: 11.

8. A pharmaceutical composition comprising the monoclonal antibody of claim 7.

9. A method of inhibiting migration of a human cell through a basement membrane matrix in a subject in need thereof, comprising administering to the subject the pharmaceutical composition of claim 8.

10. A host cell expressing the monoclonal antibody of claim 7.

11. A method of killing a cell expressing human IL-1 alpha, comprising contacting the cell with the monoclonal antibody of claim 7.

12. A method of increasing Intercellular Adhesion Molecule 1 (ICAM1) and E-Selectin expression in human endothelial cells, comprising contacting the human endothelial cells with the monoclonal antibody of claim 7.

\* \* \* \* \*

SEQUENCE LISTING

```
<160> NUMBER OF SEQ ID NOS: 12

<210> SEQ ID NO 1
<211> LENGTH: 471
<212> TYPE: PRT
<213> ORGANISM: homo sapiens
```

<400> SEQUENCE: 1

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Thr Ala Ser Gly Phe Thr Phe
            35                  40                  45

Ser Met Phe Gly Val His Trp Val Arg Gln Ala Pro Gly Lys Gly Leu
    50                  55                  60

Glu Trp Val Ala Ala Val Ser Tyr Asp Gly Ser Asn Lys Tyr Tyr Ala
65                  70                  75                  80

Glu Ser Val Lys Gly Arg Phe Thr Ile Ser Arg Asp Asn Ser Lys Asn
                85                  90                  95

Ile Leu Phe Leu Gln Met Asp Ser Leu Arg Leu Glu Asp Thr Ala Val
            100                 105                 110

Tyr Tyr Cys Ala Arg Gly Arg Pro Lys Val Val Ile Pro Ala Pro Leu
            115                 120                 125

Ala His Trp Gly Gln Gly Thr Leu Val Thr Phe Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Gln Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Leu Glu Trp Glu Ser Asn Gly Gln Pro Glu Asn Asn Tyr Lys
                405                 410                 415
```

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 2
<211> LENGTH: 1416
<212> TYPE: DNA
<213> ORGANISM: Homo sapiens

<400> SEQUENCE: 2

| | | | | | |
|---|---|---|---|---|---|
| atggagttcg | ggctgagttg | ggtgttcctg | gtggctctgc | tgcggggcgt | gcagtgccag | 60 |
| gtgcagctgg | tggagagtgg | gggtggcgtg | gtgcagcctg | ccggtctctc | tgcgcctgtct | 120 |
| tgcactgcct | ccggttttac | cttttctatg | tttggtgtgc | actgggtgcg | ccaggctccc | 180 |
| ggcaagggac | tggaatgggt | ggccgccgtg | agttacgacg | gtccaacaa | atattacgct | 240 |
| gagagcgtga | aggcagatt | caccatcagc | agagataatt | ccaagaatat | tctgttcctg | 300 |
| cagatggaca | gtctgagact | ggaggacact | gctgtgtact | actgcgctcg | tgacgccct | 360 |
| aaggtggtca | tccccgcccc | cctggcacat | tggggccagg | gaactctggt | gacctttct | 420 |
| agcgctagca | ccaagggccc | atcggtcttc | cccctggcac | cctcctccaa | gagcacctct | 480 |
| gggggcacag | cggccctggg | ctgcctggtc | aaggactact | tccccgaacc | ggtgacggtg | 540 |
| tcgtggaact | caggcgccct | gaccagcggc | gtccacacct | tcccggctgt | cctacagtcc | 600 |
| tcaggactct | actccctcag | cagcgtagtg | accgtgccct | ccagcagctt | gggcacccag | 660 |
| acctacatct | gcaacgtgaa | tcacaagccc | agcaacacca | aggtggacaa | gaaagttgag | 720 |
| cccaaatctt | gtgacaaaac | tcacacatgc | ccaccgtgcc | cagcacctga | actcctgggg | 780 |
| ggaccgtcag | tcttcctctt | cccccaaaa | cccaaggaca | ccctcatgat | ctcccggacc | 840 |
| cctgaggtca | catgcgtggt | ggtggacgtg | agccacgaag | accctgaggt | caagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | cccccatcga | gaaaaccatc | 1080 |
| tccaaagcca | aagggcagcc | ccgagaacca | caggtgtaca | ccctgccccc | atcccgggat | 1140 |
| gagctgacca | agaaccaggt | cagcctgacc | tgcctggtca | aaggcttcta | tcccagcgac | 1200 |
| atcgccctgg | agtgggagag | caatgggcag | ccggagaaca | actacaagac | cacgcctccc | 1260 |
| gtgctggact | ccgacggctc | cttcttcctc | tacagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctcctt | aagtccggga | aaataa | | | 1416 |

<210> SEQ ID NO 3
<211> LENGTH: 235
<212> TYPE: PRT
<213> ORGANISM: Homo sapiens

<400> SEQUENCE: 3

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Lys Pro Gly Lys
    50                  55                  60

Ala Pro Lys Leu Leu Ile Tyr Glu Ala Ser Asn Leu Glu Thr Gly Val
65                  70                  75                  80

Pro Ser Arg Phe Ser Gly Ser Gly Ser Asp Phe Thr Leu Thr
                85                  90                  95

Ile Ser Ser Leu Gln Pro Glu Asp Phe Ala Thr Tyr Tyr Cys Gln Gln
            100                 105                 110

Thr Ser Ser Phe Leu Leu Ser Phe Gly Gly Gly Thr Lys Val Glu His
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 4
<211> LENGTH: 708
<212> TYPE: DNA
<213> ORGANISM: Homo sapiens

<400> SEQUENCE: 4
atggacatgc gcgtgcccgc ccagctgctg gggctgctgc tgctgtggtt ccctggatct      60
aggtgcgaca ttcagatgac ccagtccccc agctcagtgt cagcctccgt gggcgacaga    120
gtgacaatca cctgccgcgc ctctcaggga atctctagtt ggctggcctg gtaccagcag    180
aagcctggaa aggcccccaa gctgctgatc tatgaagcct ccaacctgga gaccggcgtg    240
ccctctcgct tcagcggctc aggctcaggc agtgatttta ctctgaccat cagctccctg    300
cagccagagg atttcgctac ttactactgc cagcagacct cttccttcct gctgtccttc    360
gggggaggca caaaggtgga gcaccgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagtt caccggtgac aaagagcttc aacaggggag agtgttag                 708

<210> SEQ ID NO 5
<211> LENGTH: 471
<212> TYPE: PRT

<213> ORGANISM: Homo sapiens

<400> SEQUENCE: 5

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Thr Ala Ser Gly Phe Thr Phe
        35                  40                  45

Ser Met Phe Gly Val His Trp Val Arg Gln Ala Pro Gly Lys Gly Leu
    50                  55                  60

Glu Trp Val Ala Val Ser Tyr Asp Gly Ser Asn Lys Tyr Tyr Ala
65                  70                  75                  80

Glu Ser Val Lys Gly Arg Phe Thr Ile Ser Arg Asp Asn Ser Lys Asn
                85                  90                  95

Ile Leu Phe Leu Gln Met Asp Ser Leu Arg Leu Glu Asp Thr Ala Val
            100                 105                 110

Tyr Tyr Cys Ala Arg Gly Arg Pro Lys Val Val Ile Pro Ala Pro Leu
        115                 120                 125

Ala His Trp Gly Gln Gly Thr Leu Val Thr Phe Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

```
Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 6
<211> LENGTH: 1422
<212> TYPE: DNA
<213> ORGANISM: Homo sapiens

<400> SEQUENCE: 6
gccaccatgg agtttggtct gtcctgggtg ttcttggtgg ctctgctgag ggggggtgcag      60 tgccaggtcc agctggtgga gtctggtggg ggagtggtgc agcctgggag atctctgcgg     120
ctgtcttgca ctgcctctgg tttcactttc tctatgtttg gtgtgcattg ggtcaggcaa     180
gcaccaggca aaggactcga gtgggtcgca gctgtgagct atgacgggtc taacaaatat     240
tacgctgagt ctgtcaaggg taggtttacc atcagccggg ataattccaa aaatatcctg     300
ttcctgcaaa tggactctct gaggctggaa gatactgcag tctactattg tgcaaggggg     360
aggccaaagg tggtgatccc cgctcccctc gctcactggg acagggaac cctggtgact     420 ttcagctctg ctagcaccaa gggccctagc gtgttcccat ggctccttc ctccaaatct     480 acttctggag gcaccgccgc cctgggatgt ctcgtgaaag attattttcc tgagcccgtc     540
accgtgagct ggaacagcgg cgccctgact agcggcgtgc acaccttcc cgcagtgctg     600 caatctagcg gcctgtactc cctgagctct gtcgtgaccg tgccctccag cagcctcgga     660
actcagacct acatctgcaa tgtcaatcat aaaccctcta ataccaaagt cgataagaag     720
gtcgaaccta atcttgcga taaaacccat acctgccccc cttgcccagc acccgaactg     780
ctgggcggtc cctctgtgtt tctgttcccc ccaaaaccca agataccct gatgatctct     840 aggaccccg aggtcacttg tgtcgtggtg gatgtgtccc acgaagatcc agaagtcaaa     900
ttcaactggt atgtggacgg ggtcgaagtg cacaacgcaa agaccaagcc tagggaggaa     960
cagtataata gcacatatag ggtggtcagc gtcctgaccg tcctgcatca ggactggctg    1020
aatggcaaag aatataagtg taaagtgtcc aacaaggccc tgccagcccc aatcgaaaag    1080
acaatctcta agccaagggg gcaaccccgg gaacctcagg tctatacact gccacctct    1140 cgggatgaac tgaccaagaa tcaggtgagc ctgacatgtc ttgtgaaggg tttttatccc    1200
tccgacattg ccgtggagtg ggagagcaat ggacaaccag aaaataacta caaaaaccaca    1260 ccccctgtgc tggactccga tggttccttc ttcctctact ctaagctgac agtggataag    1320
tctaggtggc agcaggggaa tgtgttctcc tgctctgtga tgcacgaggc actgcacaat    1380
cattatacac aaaagtctct gtctctgtct ccaggaaagt aa                       1422

<210> SEQ ID NO 7
<211> LENGTH: 234
<212> TYPE: PRT
<213> ORGANISM: Homo sapiens

<400> SEQUENCE: 7
```

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Glu Ala Ser Asn Leu Glu Thr Gly Val
65                  70                  75                  80

Pro Ser Arg Phe Ser Gly Ser Gly Ser Gly Ser Asp Phe Thr Leu Thr
                85                  90                  95

Ile Ser Ser Leu Gln Pro Glu Asp Phe Ala Thr Tyr Tyr Cys Gln Gln
            100                 105                 110

Thr Ser Ser Phe Leu Leu Ser Phe Gly Gly Gly Thr Lys Val Glu His
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 8
<211> LENGTH: 711
<212> TYPE: DNA
<213> ORGANISM: Homo sapiens

<400> SEQUENCE: 8
gccaccatgg acatgcgcgt tcctgcccag ctcctcggac tgctgctgct ttggttccca        60
ggctcccggt gtgatattca gatgacacag tctccctcct ccgtatctgc atccgtgggc       120
gacagggtca caatcacttg tagggccagc caggggatct ctagttggct cgcatggtac       180
caacaaaagc caggtaaggc tccgaaactg ctcatttacg aagctagtaa cctcgaaaca       240
ggcgtgccaa gccggtttag cggctccggt tccggttctg acttcaccct cactatttcc       300
tccctgcaac tgaggatttt gccacatat tactgtcagc aaacttcttc ttttctgctc       360
tcctttggtg ggggaactaa ggtggagcac acagtggccg cccccagcgt ctttatcttc       420
cccccaagcg atgaacagct gaagtcaggg accgccagcg tggtctgcct gctcaataat       480
ttttaccctc gcgaggctaa ggtccaatgg aaagtggata acgccctcca gagcggtaac       540
tctcaggagt ctgtcacaga gcaagacagc aaggatagca cctattccct ctccagcacc       600
ctgacactgt ctaaggccga ctacgagaaa cacaaagtgt acgcttgtga ggtgactcac       660
cagggactga gtagccctgt gacaaaatct ttcaataggg gagaatgctg a                711

<210> SEQ ID NO 9

<211> LENGTH: 471
<212> TYPE: PRT
<213> ORGANISM: Homo sapiens

<400> SEQUENCE: 9

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Thr Ala Ser Gly Phe Thr Phe
        35                  40                  45

Ser Met Phe Gly Val His Trp Val Arg Gln Ala Pro Gly Lys Gly Leu
50                  55                  60

Glu Trp Val Ala Ala Val Ser Tyr Asp Gly Ser Asn Lys Tyr Tyr Ala
65                  70                  75                  80

Glu Ser Val Lys Gly Arg Phe Thr Ile Ser Arg Asp Asn Ser Lys Asn
                85                  90                  95

Ile Leu Phe Leu Gln Met Asp Ser Leu Arg Leu Glu Asp Thr Ala Val
            100                 105                 110

Tyr Tyr Cys Ala Arg Gly Arg Pro Lys Val Val Ile Pro Ala Pro Leu
        115                 120                 125

Ala His Trp Gly Gln Gly Thr Leu Val Thr Phe Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
```

385                 390                 395                 400
Ile Ala Val Glu Trp Glu Ser Asn Gly Gln Pro Glu Asn Asn Tyr Lys
                    405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 10
<211> LENGTH: 1422
<212> TYPE: DNA
<213> ORGANISM: Homo sapiens

<400> SEQUENCE: 10
gccaccatgg agtttggtct gtcctgggtg ttcttggtgg ctctgctgag ggggtgcag        60 tgccaggtcc agctggtgga gtctggtggg ggagtggtgc agcctgggag atctctgcgg     120
ctgtcttgca ctgcctctgg tttcactttc tctatgtttg gtgtgcattg ggtcaggcaa     180
gcaccaggca aaggactcga gtgggtcgca gctgtgagct atgacgggtc taacaaatat     240
tacgctgagt ctgtcaaggg taggtttacc atcagccggg ataattccaa aaatatcctg     300
ttcctgcaaa tggactctct gaggctggaa gatactgcag tctactattg tgcaaggggg     360
aggccaaagg tggtgatccc cgctcccctc gctcactggg acagggaac cctggtgact      420 ttcagctctg ctagcaccaa gggccctagc gtgttcccat ggctccttc ctccaaatct      480 acttctggag gcaccgccgc cctgggatgt ctcgtgaaag attattttcc tgagcccgtc     540
accgtgagct ggaacagcgg cgccctgact agcggcgtgc acacctttcc cgcagtgctg     600
caatctagcg ggctgtactc cctgagctct gtcgtgaccg tgccctccag cagcctcgga     660
actcagacct acatctgcaa tgtcaatcat aaaccctcta ataccaaagt cgataagagg     720
gtcgaaccta atcttgcga taaaacccat acctgccccc cttgcccagc acccgaactg     780
ctgggcggtc cctctgtgtt tctgttcccc ccaaaaccca agataccct gatgatctct      840 aggacccccg aggtcacttg tgtcgtggtg gatgtgtccc acgaagatcc agaagtcaaa     900
ttcaactggt atgtggacgg ggtcgaagtg cacaacgcaa agaccaagcc tagggaggaa     960
cagtataata gcacatatag ggtggtcagc gtcctgaccg tcctgcatca ggactggctg    1020
aatggcaaag aatataagtg taaagtgtcc aacaaggccc tgccagcccc aatcgaaaag    1080
acaatctcta agccaagggg gcaacccgg gaacctcagg tctatacact gccaccctct     1140
cgggaggaaa tgaccaagaa tcaggtgagc ctgacatgtc ttgtgaaggg ttttatccc     1200 tccgacattg ccgtggagtg ggagagcaat ggacaaccag aaaataacta caaaaccaca    1260
ccccctgtgc tggactccga tggttccttc ttcctctact ctaagctgac agtggataag    1320
tctaggtggc agcaggggaa tgtgttctcc tgctctgtga tgcacgaggc actgcacaat    1380
cattatacac aaaagtctct gtctctgtct ccaggaaagt aa                       1422

<210> SEQ ID NO 11
<211> LENGTH: 236
<212> TYPE: PRT
<213> ORGANISM: Homo sapiens

<400> SEQUENCE: 11

```
Met Asp Met Arg Val Pro Ala Gln Leu Leu Gly Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Glu Ala Ser Asn Leu Glu Thr Gly Val
65              70                  75                  80

Pro Ser Arg Phe Ser Gly Ser Gly Ser Gly Ser Asp Phe Thr Leu Thr
                85                  90                  95

Ile Ser Ser Leu Gln Pro Glu Asp Phe Ala Thr Tyr Tyr Cys Gln Gln
            100                 105                 110

Thr Ser Ser Phe Leu Leu Ser Phe Gly Gly Gly Thr Lys Val Glu His
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 12
<211> LENGTH: 717
<212> TYPE: DNA
<213> ORGANISM: Homo sapiens

<400> SEQUENCE: 12

```
gccaccatgg acatgcgcgt cctgcccag ctcctcggac tgctgctgct ttggttccca      60
ggctcccggt gtgatattca gatgacacag tctccctcct ccgtatctgc atccgtgggc    120
gacagggtca caatcacttg tagggccagc caggggatct ctagttggct cgcatggtac    180
caacaaaagc caggtaaggc tccgaaactg ctcatttacg aagctagtaa cctcgaaaca    240
ggcgtgccaa gccggtttag cggctccggt tccggttctg acttcaccct cactatttcc    300
tccctgcaac ctgaggattt tgccacatat tactgtcagc aaacttcttc ttttctgctc    360
tcctttggtg gaggaactaa ggtggagcac aagcggacag ttgctgctcc tagcgtcttt    420
atcttccctc caagcgatga acagctgaag tcagggaccg ccagcgtggt ctgcctgctc    480
aataatttt accctcgcga ggctaaggtc aatggaaag tggataacgc cctccagagc    540
ggtaactctc aggagtctgt cacagagcaa gacagcaagg atagcaccta tccctctcc    600
agcaccctga cactgtctaa ggccgactac gagaaacaca agtgtacgc ttgtgaggtg    660
actcaccagg gactgagtag ccctgtgaca aaatctttca ataggggaga atgctga      717
```